United States Patent [19]

Hausselt et al.

[11] Patent Number: 4,606,887

[45] Date of Patent: Aug. 19, 1986

[54] COBALT ALLOYS FOR THE PRODUCTION OF DENTAL PROTHESIS

[75] Inventors: Jürgen Hausselt, Langenselbold; Dieter Kaufmann, Birstein; Udo Englisch, Rodenbach, all of Fed. Rep. of Germany

[73] Assignee: Degussa Aktiengesellschaft, Frankfurt, Fed. Rep. of Germany

[21] Appl. No.: 614,140

[22] Filed: May 25, 1984

[30] Foreign Application Priority Data

May 28, 1983 [DE] Fed. Rep. of Germany ....... 3319457

[51] Int. Cl.$^4$ ............................................. C22C 19/07
[52] U.S. Cl. ..................................... 420/437; 420/438
[58] Field of Search ............... 420/435, 436, 437, 438; 148/408, 425

[56] References Cited

U.S. PATENT DOCUMENTS

| | | | |
|---|---|---|---|
| 3,399,058 | 8/1968 | Roush | 420/435 |
| 3,948,653 | 4/1976 | Test et al. | 420/445 |
| 4,229,215 | 10/1980 | Prosen | 420/440 |
| 4,255,190 | 3/1981 | Prosen | 420/440 |
| 4,263,045 | 4/1981 | Prosen | 420/440 |

FOREIGN PATENT DOCUMENTS

| | | |
|---|---|---|
| 000513 | 10/1979 | European Pat. Off. . |
| 2432014 | 1/1975 | Fed. Rep. of Germany . |
| 2538099 | 4/1976 | Fed. Rep. of Germany . |
| 2258547 | 7/1976 | Fed. Rep. of Germany . |
| 3001126 | 1/1981 | Fed. Rep. of Germany . |
| 3038036 | 5/1981 | Fed. Rep. of Germany . |

*Primary Examiner*—R. Dean
*Attorney, Agent, or Firm*—Cushman, Darby & Cushman

[57] ABSTRACT

As replacements for noble metal containing alloys fused to porcelain in dental prosthetics there are needed alloys based on cobalt-chromium-tungsten which have a hardness of less than 300 (HV 5), can be veneered faced with known dental ceramics without problems and can be worked without problem with the customary working techniques. Such alloys contain in addition to 42–69.5 weight % cobalt, 10–35 weight % chromium, and 5–25 weight % tungsten, 2–10 weight % iron, 1–4 weight % aluminum, 0–5 weight % rhenium, and 0–2 weight % titanium, whereby the sum of the content oc chromium, tungsten, and rhenium is between 27.5 and 45 weight % and the sum of aluminum and titanium is below 5 weight %.

15 Claims, No Drawings

COBALT ALLOYS FOR THE PRODUCTION OF DENTAL PROTHESIS

BACKGROUND OF THE INVENTION

The invention is directed to cobalt alloys for the production of fixed and removable dental constructions consisting of (or consisting essentially of) 42 to 69.5 weight % cobalt, 10 to 35 weight % chromium, and 5 to 25 weight % tungsten.

For a long time there have been approved for the production of crowns, bridges, and inlays for restorative dentistry noble metal alloys based on gold, platinum, palladium, and silver. This is especially true for the so-called porcelain fused to metal alloys in which for esthetic reasons, the metallic crowns and bridges are entirely or partially veneered with tooth colored ceramics.

However, for reasons of cost for many years they have given way to an increasing extent to non-noble metal alloys. The great majority of these alloys are so-called Ni based alloys which in addition to nickel, contain as an essential additive chromium for the production of a sufficient resistance to corrosion and oxidation. The composition of such alloys is known, for example, from European Pat. No. 5013, German OS 2432014, German OS 2538099, German OS 2528547, and U.S. Pat. No. 3,948,653.

Recently, however, doubts have been exposed in increasing measure to the use of nickel based alloys which doubts are caused by the known allergic action of nickel or the known or believed carcinogenic action of nickel dusts or nickel compounds (see MAK-Werte-Liste der Berufsgenossenschaft der Chemischen Industrie 1979 and S. S. Brown, F. W. Sundermann; "Nickel Toxicoloty," Academic Press, London 1980).

Cobalt based alloys have proven good in dental medicine for many years, for example, for the production of cast palate plates for removable dental structures. Allergic reactions have not been known by patients who wear this type of prothesis. Therefore there have not been a lack of attempts to also produce crowns and bridges for the complete or partial veneering made of cobalt alloys with ceramics.

A series of requirements are placed on the so-called fired on alloys.

Paramount among these is a thermal expansion and contraction behavior which is balanced to the type of dental ceramic used, which customarily is fused on the metallic framework in several layers at about 950° C. to 1000° C. A second essential requirement of dental porcelain fused to metal alloys is that the alloys are not too hard. Alloys having hardnesses of about 300 (HV 5) lead to considerable difficulties in separating, grinding, milling, and polishing in dental laboratories and therefore to increased wear of the work tools and longer time requirements which can partially or completely eliminate the price advantages compared to noble metal alloys. Furthermore, alloys having hardnesses of more than about 300 (HV 5) can no longer be regarded as physiologically compatible. Frequently; in the side tooth area crowns and bridges are not completely veneered In order to protect the antagonists before there is too high an abrasion, the masticating surfaces should not be veneered with the very hard ceramics. This mode of action from experience is only meaningful if the hardness of the unveneered metallic masticating surfaces are clearly below 300 (HV 5).

Further important requirements of alloys fused to dental porcelain are that the alloys be meltable and castable easily and without problem in the casting apparatus customary in the dental laboratory. This means that dental alloys must be meltable and castable, e.g. with gas burners, inductive high frequency casting apparatus, electric arc melting apparatuses and suitable electrically heated casting devices. Therefore alloys which because of their compositions, can only be melted and cooled under a vacuum or protective gas, e.g. perhaps only in very specific and expensive crucible materials are not practical. A good form filling and flow behavior of the alloys in connection with the castability still has a special role because crowns and bridges in part must have a very filigree form. Additional decisive requirements are good solderability and a good exact fitting of the cast objects.

A good adhesion to the ceramic which must guarantee an internal union between the two material components which withstands all loads also is of great significance for dental porcelain fused to alloys.

All previously known cobalt alloys contain in addition to cobalt as the main component chromium as well as secondary components, molybdenum, and/or tungsten as well as additional elements. Examples of tungsten containing alloys are found in U.S. Pat. Nos. 4,229,215; 4,263,045; 4,255,190,; and 4,253,869, and in German OS 3001126 and 3038036.

In several of the mentioned alloys there are specified as essential components noble metals such as ruthenium.

However, all known dental porcelain fused to alloys based on cobalt have in part considerable inadequacies in one or more of the essential properties mentioned for dental porcelain fused to alloys. This is especially true in regard to their compatability with known types of veneering ceramics and their hardness. Thus all known fused to procelain alloys based on cobalt show hardnesses of at least about 300 (HV 5) and in some cases, of over 450 (HV 5). Many of the known cobalt fused to porcelain alloys when used with specific types of ceramics moreover, especially with rapid cooling from firing temperature (about 960° C. to 1000° C.) lead to cracks in the ceramic. With many known cobalt alloys fused to porcelain, moreover, the adhesion between alloy and ceramic is not sufficient so that frequently it is necessary to use adhesive materials.

Therefore, it was the problem of the present invention to develop cobalt alloys for the production of fused and removable dental constructions containing (or consisting essentially of) 42 to 69.5 weight % cobalt, 10 to 35 weight % chromium, and 5 to 25 weight % tungsten which have hardnesses of clearly less than 300 (H V5) after the heat treatment necessary for the veneering with ceramic, which are fused to the known types of ceramics in crack-free and well adhering manner and which can be worked in problem-free and simple manner with the customary methods of working and apparatuses in the dental laboratory.

SUMMARY OF THE INVENTION

This problem was solved according to the invention by additionally including in the alloys 2–10 weight % iron, 1–4 weight % aluminum, 0–5 weight %, e.g. 0.2–5 weight % rhenium, and 0–2 weight %, e.g. 0.2–2 weight % titanium whereby the sum of the contents of chromium, tungsten, and rhenium is at least 27.5 weight % and at most 45 weight % and the sum of titanium and aluminum is at most 5 weight %. Furthermore, the alloy can contain 0.01–0.2 weight % boron, 0.01–0.2 weight % yttrium, 0.2–2 weight % silicon, 0.1–4 weight % copper, and 0.1–1.3 weight % tin.

Preferably the alloys contain not over 40 weight % chromium, tungsten, and rhenium.

Surprisingly it has been found that adding alloying elements of 2–10 weight % iron and 1–4 weight % titanium to ternary cobalt-chromium-tungsten alloys having 42 to 69.5 weight % cobalt, 10–35 weight % chromium, and 5–25 weight % tungsten clearly lowers the hardness of these alloys and thereby simultaneously positively influences the remaining essential properties for dental fired on alloys (i.e. alloys fused to dental porcelain), such as melting and casting behavior, behavior with dental ceramic compositions or workability.

This is the more surprising since aluminum customarily worsens the meltability of alloys in air and increases the hardness and tensile strength through the formation of an intermetallic cobalt-aluminum phase (Cobalt-Base Superalloys 1970, Cobalt Monograph Series, Centre a' Information du Cobalt Brussels, page 21). It has been found that iron and aluminum, each by itself, lowers the hardness value when included in the alloy with the mentioned ternary starting alloy. However, with aluminum contents beginning about 4 weight % the hardness of the alloys increases again and with alloys beginning with an iron content of about 10 weight %, the thermal expansion value becomes more than about $15 \times 10^{-6} K^{-1}$ so that the best properties can be produced through addition of 2–10 weight % iron and 1–4 weight % aluminum to cobalt-chromium-tungsten alloys having a total ternary range of 42–69.5 weight % cobalt, 10–35 weight % chromium, and 5–25 weight % tungsten.

Alloys having contents of chromium, tungsten, and rhenium between 27.5 and 40 weight % are especially advantageous because in this range there is observed a very good resistance to corrosion with simultaneously better workability in dental techniques.

Titanium in the region up to about 2 weight % shows a similar cation but not quite as positive as aluminum so that the alloys of the invention in addition to aluminum also can contain up to 2 weight % titanium. It has further been found that aluminum and titanium together should not exceed 5 weight % because otherwise the hardness increases again and the melting behavior in air becomes worse.

Further investigation have shown that tungsten can be partially replaced by rhenium without the properties of the alloys deteriorating. Small rhenium contents rather improve the extensibility of the alloys.

The adhesion of the alloys of the invention rather is improved by including small contents of rhenium.

The adhesion of the alloys of the invention to dental ceramics is good. With small additions of yttrium, between 0.01 and 0.2 weight %, the adhesion can be still further improved.

The hardness of the alloys can be still further lowered by adding tin in an amount up to about 1.5 weight %, e.g. 0.1–1.5 weight %, without impairing the remaining properties. This is especially surprising for the reson that according to the state of the art (Cobalt-Base Superalloys, 1970, page 5) tin is considered as a poison in nickel and cobalt based alloys because already in traces beginning with 20 ppm, it exerts very bad effects. The tin content in the alloys of the invention should not exceed 1.5 weight % because otherwise the alloys are inclined to brittleness.

Also copper in contents up to 4 weight %, e.g. 0.1–4 weight %, effects a trifling reduction in hardness. If it is desired to lower the Liquidus temperature of the alloys of the invention, which depending on the composition is between about 1360° C. and about 1420° C., then this can be attained through small additions of boron, e.g. 0.01–0.2 weight % and/or silicon, e.g. 0.1–2 weight %.

By addition of boron and silicon the hardness increases again so that the alloys of the invention in no case should contain more than 0.2 weight % boron and/or 2 weight % silicon.

All known cobalt-chromium alloys for porcelain fused to metal operation clearly contain more chromium than tungsten or molybdenum. Customarily the ratio of chromium, tungsten or of chromium, molybdenum is about 3:1 to about 6:1. Unexpectedly it has now been found that the alloys have particularly favorable properties if the content of chromium and of tungsten plus rhenium is present in approximately the same amount, if thus the ratio of chromium (tungsten and rhenium) is between about 2:3 and about 2:1 and preferably between about 3:2 and about 2:3. In a particularly preferred form the ratio of chromium: tungsten in the alloys is between about 4:3 and about 3:4 whereby the content of chromium plus tungsten makes up between 30 and 40 weight %.

There are obtained especially good properties with alloys having the following composition.

50 to 65 weight % Cobalt
15 to 22 weight % Chromium,
15 to 22 weight % Tungsten,
3 to 7 weight % Iron, and
1 to 3 weight % Aluminum The composition can consist essentially of or consist of the stated materials.

Unless otherwise indicated all parts and percentages are by weight.

DETAILED DESCRIPTION

The following table shows the main properties of several illustrative cobalt alloys.

TABLE

| Nr. | Co | Cr | W | Re | Fe | Al | Ti | Other | Melting Range $T_l/T_s$ °C. | Coefficient of Expansion $\times 10^{-6}/K$ | Hardness HV5 |
| --- | --- | --- | --- | --- | --- | --- | --- | --- | --- | --- | --- |
| 1 | 55.6 | 20.0 | 16.4 | — | 6.5 | 1.5 | — | — | 1414/1380 | 14.8 | 251 |
| 2 | 55.2 | 16.4 | 20.35 | — | 6.5 | 1.5 | — | Y 0.05 | 1416/1380 | 14.8 | 246 |
| 3 | 53.6 | 17.7 | 17.7 | — | 7.5 | 3.5 | — | — | 1370/1350 | 14.7 | 282 |
| 4 | 54.9 | 18.2 | 18.2 | 0.2 | 5.8 | 2.0 | 0.2 | Sn 0.5 | 1410/1370 | 14.5 | 239 |
| 5 | 51.5 | 23.0 | 16.0 | — | 5.5 | 2.0 | — | Cu 2, | 1420/1350 | 14.9 | 270 |
| 6 | 61.0 | 19.0 | 13.75 | — | 4.0 | 1.0 | — | Cu 1, B 0.05, Si 0.2 | 1410/1374 | 14.8 | 290 |

TABLE-continued

| Nr. | Co | Cr | W | Re | Fe | Al | Ti | Other | Melting Range $T_l/T_s$ °C. | Coefficient of Expansion $\times 10^{-6}$/K | Hardness HV5 |
|---|---|---|---|---|---|---|---|---|---|---|---|
| 7 | 54.2 | 18.4 | 16.4 | 3.0 | 5.7 | 2.3 | — | — | 1420/1390 | 14.7 | 280 |
| 8 | 54.9 | 17.8 | 17.8 | — | 6.0 | 2.0 | — | Sn 0.5, Cu 1.0 | 1400/1365 | 14.6 | 228 |
| 9 | 55.2 | 30.2 | 7.0 | — | 6.2 | 1.4 | — | — | 1415/1382 | 14.8 | 288 |
| 10 | 57.6 | 18.0 | 17.0 | 0.2 | 5.0 | 1.2 | 1.0 | — | 1410/1388 | 14.7 | 279 |

The entire disclosure of German priority application P 3319457.2 is hereby incorporated by reference.

What is claimed is:

1. A cobalt alloy suitable for the production of fixed and removable dental constructions consisting essentially of 50 to 65 weight % cobalt, 15–22 weight % chromium, and 5–15 weight % tungsten, 3–7 weight % iron, 1–3 weight % aluminum, 0–5 weight % rhenium, and 0–2 weight % titanium, whereby the sum of the contents of chromium, tungsten, and rhenium is at least 27.5 weight % and at most 45 weight % and the sum of titanium and aluminum is at most 5 weight %.

2. A cobalt alloy according to claim 1 consisting of the stated materials.

3. A cobalt alloy according to claim 1 containing 0.2–5 weight % rhenium.

4. A cobalt alloy according to claim 1 containing 0.2–2 weight % titanium.

5. A cobalt alloy according to claim 1 also including at least one of the elements 0.01–0.2 weight % boron, 0.01–0.2 weight % yttrium, 0.1–2 weight % silicon, 0.1–4 weight % copper, and 0.1–1.5 weight % tin.

6. A cobalt alloy according to claim 5 which contains not over 40 weight % chromium, tungsten, and rhenium.

7. A cobalt alloy according to claim 1 which contains not over 40 weight % chromium, tungsten, and rhenium.

8. A cobalt alloy according to claim 7 wherein the ratio of chromium to tungsten plus rhenium is between about 2:3 and about 2:1.

9. A cobalt alloy according to claim 6 wherein the ratio of chromium to tungsten plus rhenium is between about 2:3 and about 2:1.

10. A cobalt alloy according to claim 5 wherein the ratio of chromium to tungsten plus rhenium is between about 2:3 and about 2:1.

11. A cobalt alloy according to claim 1 wherein the ratio of chromium to tungsten plus rhenium is between about 2:3 and about 2:1.

12. A cobalt alloy according to claim 9 wherein the ratio of chromium to tungsten plus rhenium is between about 2:3 and about 3:2.

13. A cobalt alloy according to claim 8 wherein the ratio of chromium to tungsten plus rhenium is between about 2:3 and 3:2.

14. A cobalt alloy according to claim 13 wherein the content of chromium plug tungsten is at least 30 weight % and at most 40 weight % and the ratio of chromium to tungsten between about 3:4 and about 4:3.

15. A cobalt alloy according to claim 12 wherein the content of chromium plus tungsten is at least 30 weight % and at most 40 weight % and the ratio of chromium to tungsten between about 3:4 and about 4:3.

* * * * *